(12) United States Patent
Wong

(10) Patent No.: US 7,259,374 B2
(45) Date of Patent: Aug. 21, 2007

(54) METHOD FOR DETECTING A GAS SPECIES USING A SUPER TUBE WAVEGUIDE

(75) Inventor: Jacob Y. Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

(21) Appl. No.: 11/317,264

(22) Filed: Dec. 23, 2005

(65) Prior Publication Data

US 2007/0145275 A1    Jun. 28, 2007

(51) Int. Cl.
*G01J 5/02* (2006.01)

(52) U.S. Cl. .................. 250/339.13; 358/437

(58) Field of Classification Search .......... 250/339.13; 356/437

See application file for complete search history.

(56) References Cited

U.S. PATENT DOCUMENTS 5,060,508 A * 10/1991 Wong ........................ 73/31.02
5,696,379 A    12/1997 Stock
5,747,808 A *  5/1998 Wong ........................ 250/343
5,886,348 A *  3/1999 Lessure et al. ........ 250/339.13
6,527,398 B1 *  3/2003 Fetzer ....................... 356/437
6,818,895 B2 * 11/2004 Williams .................... 250/343

* cited by examiner

*Primary Examiner*—David Porta
*Assistant Examiner*—Jessica L. Eley
(74) *Attorney, Agent, or Firm*—Roy L Anderson; Wagner, Anderson & Bright LLP

(57) ABSTRACT

A method for detecting the concentration of one or more gas species by using infrared radiation emitted from one or more sources into a sample cell which is a hollow waveguide with multiple bends collectively greater than 180 degrees in three dimensions, the infrared radiation being quasi-focused into a beam with an angle of incidence between greater than approximately 0° and approximately 10° relative to a longitudinal axis of a first linear segment of the sample cell proximate the source, then detecting two or more signals in which one of the signals is used to compensate for water vapor. The methods can detect gas concentrations down to 1 ppm or less.

20 Claims, 8 Drawing Sheets

METHOD FOR DETECTING A GAS SPECIES USING A SUPER TUBE WAVEGUIDE

CROSS-REFERENCE TO RELATED APPLICATIONS

This application is related to an application filed concurrently herewith, with the same inventor, entitled "Ultra-High Sensitivity NDIR Gas Sensors,".

FIELD OF THE INVENTION

The present invention is in the field of gas analysis and more particularly relates to a compact and long path-length sample cell for use in measuring very small concentrations of a gas based upon the absorption of infrared radiation as it passes through the gas within the sample chamber.

BACKGROUND OF THE INVENTION

Certain gases have absorption bands in the electromagnetic spectrum that absorb so weakly that absorption can only be detected after the radiation has traveled a relatively long distance, perhaps as long as tens of meters, through the gas. In other situations the gases of interest might have adequate absorption strengths but they must be detected in very low concentrations, typically in the parts-per-million (ppm) or even in the parts-per-billion (ppb) ranges, so that long path lengths are also required in this situation. But the most challenging situation occurs when the very low concentration of a weakly absorbing gas is required to be determined. Under this circumstance the need for a very long path-length sample chamber is absolutely indispensable.

Although numerous gas detection methodologies have been developed over the years, the most notable ones of which include electrochemical fuel cells, Figaro or Tin Oxide ($SnO_2$) sensors, Metal oxide semiconductor (MOS) sensors, Catalytic (Platinum bead) sensors, Photo-ionization detector (PID), Flame-ionization detector (FID), Thermal Conductivity sensors etc., they are all commonly referred to as "interactive" types of gas detectors. As such almost every one of them without exception suffers from long-term drifts and non-specificity problems, particularly when applied to the detection of volatile organic compounds or VOC's. The Non-Dispersive Infrared (NDIR) technique, on the other hand, has long been considered as one of the best methods of gas measurement since the 1950s. In addition to being highly specific, NDIR gas analyzers are also very sensitive, stable, rugged, reliable, and easy to maintain. The advent of the so-called "wave-guide" sample chamber disclosed in U.S. Pat. No. 5,163,332 by Wong in 1992 and commonly referred to as simply "The Tube" significantly simplifies today's NDIR gas analyzers into compact, rugged and low-cost sensors while still maintaining their superior performance characteristics.

An even more superior gas measurement technique, which only became fully developed within the past two decades, uses the output of a laser as a coherent radiation source. It is called the Tunable Diode Laser Absorption Spectroscopy or TDLAS technique. TDLAS gas sensors in general have better gas detection sensitivity and are more compact and reliable than the corresponding NDIR counterparts. However, due to available wavelength restrictions, they have to depend upon the much weaker higher harmonics of the fundamental absorption bands of gases that they detect. Consequently, TDLAS sensors routinely require many times the path lengths required for their NDIR counterparts in order to attain the same detection sensitivities.

Practical gas analyzers for commercial use seldom incorporate very long path-length sample cells for such purposes primarily because of size limitations. Where the use of long path-length sample cells cannot be avoided, it is common to use lenses and mirrors to fold an optical beam so that the latter can traverse the sample cell a number of times in order to increase its effective path length.

A multi-path absorption cell was described by J. U. White, Journal of Optical Society of America, Volume 32, page 285 (1942). The essential parts of the White cell consist of three spherical concave mirrors all having the same radius of curvature and positioned to form an optical cavity. Over the years, utilizing the principle outlined in White's article, multi-path cells having path-lengths greater than 40 meters have been successfully constructed and even made available for public purchase. However, since the settings of the White cell has to be carefully and meticulously adjusted every time before its use in order for it to correctly provide the desired path-length, the use of White cells has been confined mainly to laboratories and they are seldom deployed for the construct of practical and transportable gas analyzers.

Another multi-path absorption cell was described by D. Herriott et al., Journal of Applied Optics, Volume 3, page 523 (1964). The Herriott cell consists of two spherical mirrors separated by nearly their radius of curvature. The optical beam is to be injected through a hole in one mirror and is reflected back and forth a number of times before exiting from the same hole. Unlike the White cell, the beam remains essentially collimated throughout its traversals of the cell. Although the Herriott cell is in principle simpler to align than the White cell since it consists of only two mirrors, the number of passes through the cell is determined by the exact mirror separation which has also to be meticulously adjusted every time before its use. Thus, like the White cell, the Herriott cell is also not robust enough for use in portable or transportable gas analyzers.

In U.S. Pat. No. 4,756,622, Wong in 1988 disclosed another approach for providing long path-lengths for measuring the weak absorption by a gas. In Wong's invention, light is made to travel through a limited volume of the gas a large number of times. The light is placed on a closed optical path on which it circulates through the gas sample. After a desired number of passes through the sample, the light is removed from the closed optical path. Introduction of the light to the closed optical path and removal therefrom is accomplished through the use of a polarizing beam-splitter and a Pockels cell located on the closed path. Light is put onto the closed path by the polarizing beam-splitter which imparts a specific polarization. During the first circuit the Pockels cell alters the polarization by 45 degrees thereby preventing the light from escaping back out through the polarizing beam-splitter. After a desired number of passes, the Pockels cell again alters the polarization by 45 degrees thereby permitting the light to be redirected out of the closed path by the polarizing beam-splitter. In this way the so-called "Wong cell" can readily achieve very long path-lengths of hundreds or even thousands of meters or more.

While the long path-length sample chamber disclosed by Wong in U.S. Pat. No. 4,756,622 is indeed compact and does not require careful and painstaking adjustments of its optical components prior to its use, it does require a rather complex and expensive component, namely the Pockels cell and its associated electronic driver, in order to make the overall scheme functional. A typical Pockels cell system comprising the cell and its electronic driver costs upwards of $10,000.00

(for example Pockels Cell System Model No. 5046 manufactured by Lasermetrics, Div. of FastPulse Technology, Inc.). Furthermore, The Pockels cell is a wavelength dependent device requiring a number of electro-optical crystals (e.g. KDP for wavelengths up to 1.33 microns and Lithium Niobate for up to 1.6-1.7 microns etc.) for its construct. Consequently, and unlike the White and Herriott cells which are wavelength independent, the use of the Wong cell is often times limited only to those instances when the appropriate Pockels cells are available with the right electro-optical crystals and having the correct optical transmission in the electromagnetic spectrum for its use.

The White and Herriott cells described above require meticulous settings prior to their uses whereas the Wong cell (U.S. Pat. No. 4,756,622 (1988)) suffers from the disadvantages of being too expensive and wavelength dependent applications due to the limited availability of suitable electro-optical materials for making the appropriate Pockels cells. Nonetheless, as the world's population continues to grow, particularly in urban areas, and the people's living environments get progressively worsened as a result of more energy consumption through the burning of more and more fossil fuels, the need to measure weak absorbing toxic gas species in very low concentrations (ppb's) such as Carbon Monoxide (CO), Nitrogen Dioxide (NO2), Ozone, volatile organic compounds (VOC's) etc., in both open and closed spaces in order to protect public's health, becomes ever more pressing. The tragic 9/11 terror attack incident exacerbated the situation even more. In order to prevent future terror attacks on the masses using extremely toxic gases such as mustard gas, sarin and other deadly nerve agents, the need to detect weakly absorbing lethal gases in the minutest amount (parts per trillion or ppt levels) accentuates the situation even more urgently than ever before. The complex and expensive long path length sample chambers proposed by various authors discussed above are clearly inadequate for use as portable and transportable gas analyzers for this type of application. Simple, rugged, low-cost and long path-length sample cells, suitable for use with both the NDIR and TDLAS type transportable gas analyzers, are, to the best of the present inventor's knowledge, not available commercially today even though they are very urgently needed. It is to this long felt need that the present invention is directed.

SUMMARY OF THE INVENTION

The present invention is generally directed to a method for detecting the concentration of a gas species X in which infrared radiation is emitted from a source into a sample cell which is a hollow waveguide with a plurality of bends that are collectively greater than 180 degrees in three dimensions, the radiation being quasi-focused into a beam with an angle of incidence between greater than approximately 0° and approximately 10° relative to a longitudinal axis of a first linear segment of the sample cell proximate the source, then detecting two signals in two detectors in a detector chamber, using the second signal to adjust the first signal for water vapor.

In a first, separate group of aspects of the present invention, the concentration of gas species X detected is less than 100 parts per million ("ppm"), or even less than 1 ppm, and the plurality of bends are collectively greater than 360 degrees in three dimensions.

In a second, separate group of aspects of the present invention, the infrared radiation is quasi-focused into the beam either by a conical reflective surface having an inclined angle to the longitudinal axis of approximately 10 degrees and the conical reflective surface is installed proximate an emitting surface of the infrared source or by a parabolic mirror, while the infrared radiation is focused (e.g., by a conical mirror with a vertical angle with respect to the longitudinal axis of the detector chamber of not more than approximately 10 degrees) after it has traveled through substantially all of the waveguide as it approaches the first detector, and possibly also between detectors spaced apart from each other.

In a third, separate group of aspects of the present invention, at least one additional gas is measured through use of a third detector and correction for water vapor. The geometry of the various detectors can be varied, and focusing between detectors can be used. Also, multiple radiation sources can be used to emit infrared radiation into the sample cell.

It is an object of the present invention to advance methods for using a compact and long path-length sample cell to measure very small concentrations of a gas based upon the absorption of infrared radiation as it passes through the gas within the sample chamber. It is a further object of the present invention to advance methods that can use such a sample cell to detect very low quantities of a sample gas in an economical manner.

The novel features which are believed to be characteristic of the invention, both as to construction and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
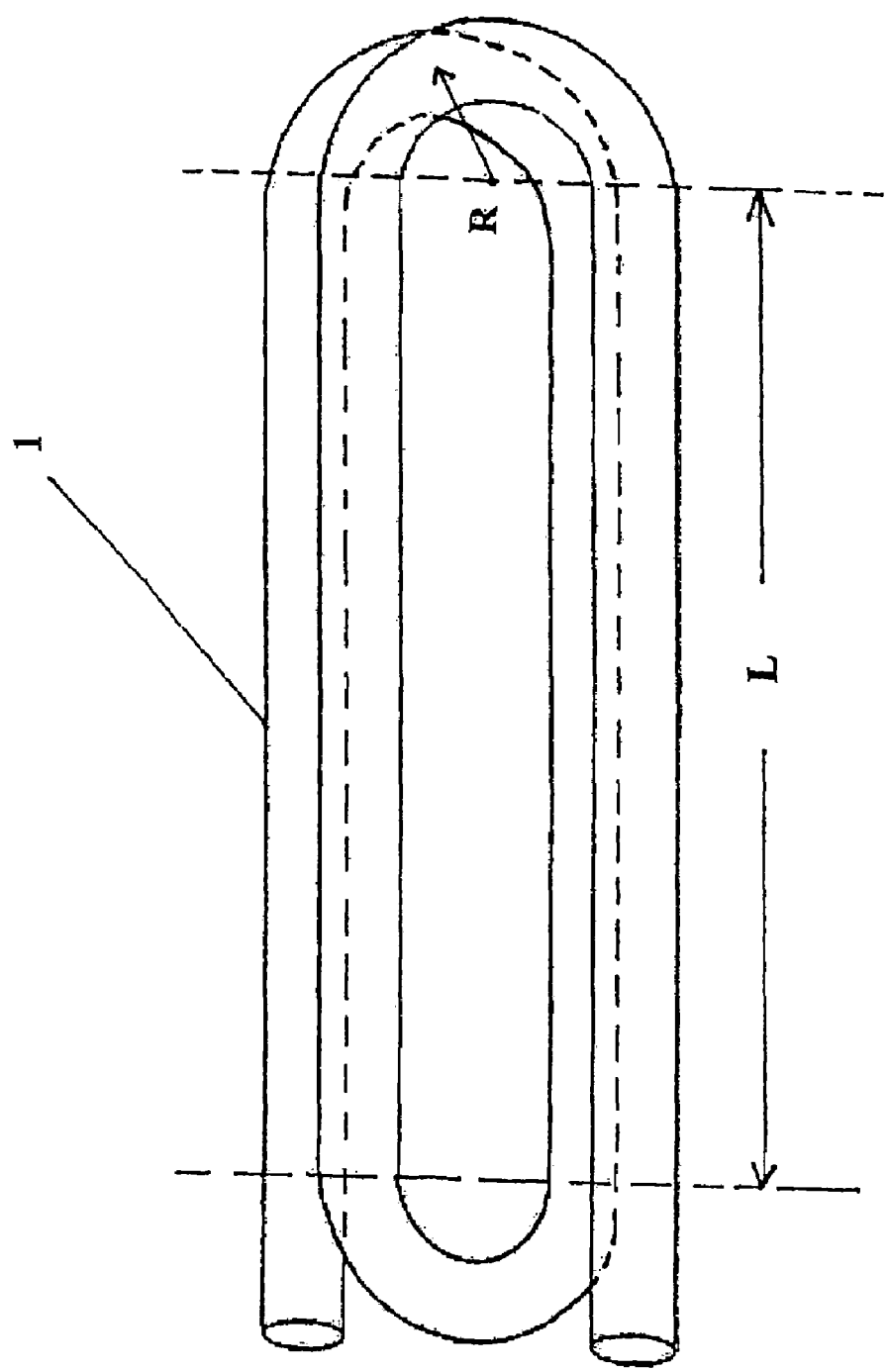
FIG. 1 is a schematic layout drawing for the present Super Tube invention showing a bending angle of 540° from the original orientation with three U (180°) turns.

For over two decades, the present inventor diligently worked on simple, rugged and low-cost NDIR gas sample chambers culminating in the so-called "wave-guide" sample chamber invention disclosed in U.S. Pat. No. 5,163,332 (1992). Indeed, for gases with moderate to strong absorption bands in the mid-infrared spectral region like $CO_2$ (4.26 μm), $H_2O$ (2.7 μm), $CH_4$ (3.4 μm) etc., the optimum and simplest gas sample chamber is a hollow straight metallic tube with arbitrary cross-section but speculatively reflective inner walls very much likened to a standard microwave wave-guide. Today after over a decade has gone by since the advent of the "wave-guide" gas sample chamber (a.k.a., "The Tube"), most of the reliable, rugged, sensitive and low-cost $CO_2$ sensors use this design, rendering a host of new applications, including faster and false-alarm resistant fire detectors and Demand Control Ventilation (DCV) strategies for saving energy in high-rise office and commercial buildings, many of which were not practical earlier because of high $CO_2$ sensor costs.

The present invention discloses a new sample chamber that, like the prior "wave-guide" or The Tube, will create a host of new applications because it overcomes a number of technical impediments that have prevented the extension of such an approach into the arena of achieving compact, low-cost and long path-length NDIR and TDLAS gas sample chambers.

In U.S. Pat. No. 5,696,379 issued to Burkhard Stock in 1997, a two-dimensional configuration for a waveguide type NDIR gas sample chamber aimed at reducing the size of the subsequent gas sensor was disclosed. In this disclosure, a configuration utilizing two 90° bends and one with one 90° bend followed by a U-shape in one plane were described for achieving the overall size reduction for the designed NDIR gas sensors. Without an explicit description or reasoning, the author of this patent also claimed that his 2-dimensional configuration can also be extended to the third dimension with equal benefits. However, he emphasized with a detailed explanation that his teaching only worked for guiding the radiation through a maximum of a 180° bend such as two right angle (90°) bends or a U (180°) bend. Also, standard radiation sources (quasi blackbody) were used but no method teaching how to guide the emitted radiation down the two-dimensional hollow waveguide was advanced. There is no doubt that the use of curved hollow waveguides with speculatively reflective inner walls will render the design of an NDIR gas sensor more compact than the use of a straight hollow waveguide having the same path length. However, the gain in compactness for the designed gas sensor using either a 2- or 3-dimensionnal hollow waveguide configuration is severely limited by not being able to guide the radiation through a bend that is greater than 180°.

Contrary to the disclosure of U.S. Pat. No. 5,696,379 issued to Stock (1997), the current invention is a 3-dimensional configuration such as the shape of a many-turn circular coil (>360°) or a number of paper clip-shaped tubes stacked together to create a column by deforming the shape of the circular tube forming the coil into an elongated ellipse. The current invention called the "Super Tube" exploits the curved hollow waveguide concept in three dimensions by advancing methods to allow radiation to readily propagate through bends that are >180° thereby achieving a very long path length sample chamber that occupies the minimum of a 3-dimensional space, even though Stock teaches away from such a result.

The first problem that the present invention addresses is to make sure that the incident radiation entering a long waveguide sample chamber having many curves (such as a coil) or U-bends (in the form of a stack of paper clips) be able to "turn" corners inside with relative ease and thereby exiting without significant loss in radiation intensity. The present invention solves this first problem by reducing the angles of incidence for radiations emanating from a quasi-blackbody infrared source.

The second problem that the present invention addresses is to restore some of the inevitable losses that the radiation suffers as it traverses the 3-dimensioanl curved hollow tube or the "Super Tube." The current invention addresses this problem with simple internal focusing elements installed inside the Super Tube. This is unique only to the innate structure of the current invention.

The third problem that the present invention addresses is the interference of the measurement by ubiquitous water vapor that can be present in the atmosphere in relatively small amounts (e.g. 5,000 ppm) on a dry day or in significantly larger quantities (>45,000 ppm) on a humid day. The current invention addresses this problem with a novel technique of in-situ water vapor correction.

The main drawback for the present invention is the fact that the path-length of the sample chamber is no longer adjustable but depends only upon the actual length of the Super Tube. Comparing with the White and the Herriott cells, the present invention does not require any meticulous adjustments of the optical components prior to its use. It does not require any expensive component like the Pockels cell in the Wong cell which also limits its use by virtue of available electro-optical crystals for its construction. Furthermore, the Super Tube is very easy to build and at a significantly lesser cost. Finally, it is rugged enough for use outside of laboratories in both NDIR and TDLAS type transportable gas analyzers.

The Super Tube of the present invention is a hollow metallic tube, preferably made out of aluminum, brass or stainless steel with specularly reflective inner walls. The typical outside diameter for the Super Tube is not critical and a convenient value is 0.500" with a typical wall thickness of ~0.050". FIG. 1 depicts the schematic layout for the present Super Tube 1 invention having a bending radius of "R" and a section length of "L". The total path length for the Super Tube is equal to $[(N \times \pi \times R)+(N+1) \times L]$ where N is the number of "U" (180°) bends forming the Super Tube. The bending radius R typically should be >1.00" otherwise it would be very difficult to form. The sectional length L can be of any value that fits a particular dimensional requirement. As shown in FIG. 1 the path length has a value equal to $(3\pi R+4L)$. For example, when R=1.25" and L=12", the path length of the Super Tube will be approximately 2 meters or six feet.

Figure 2:
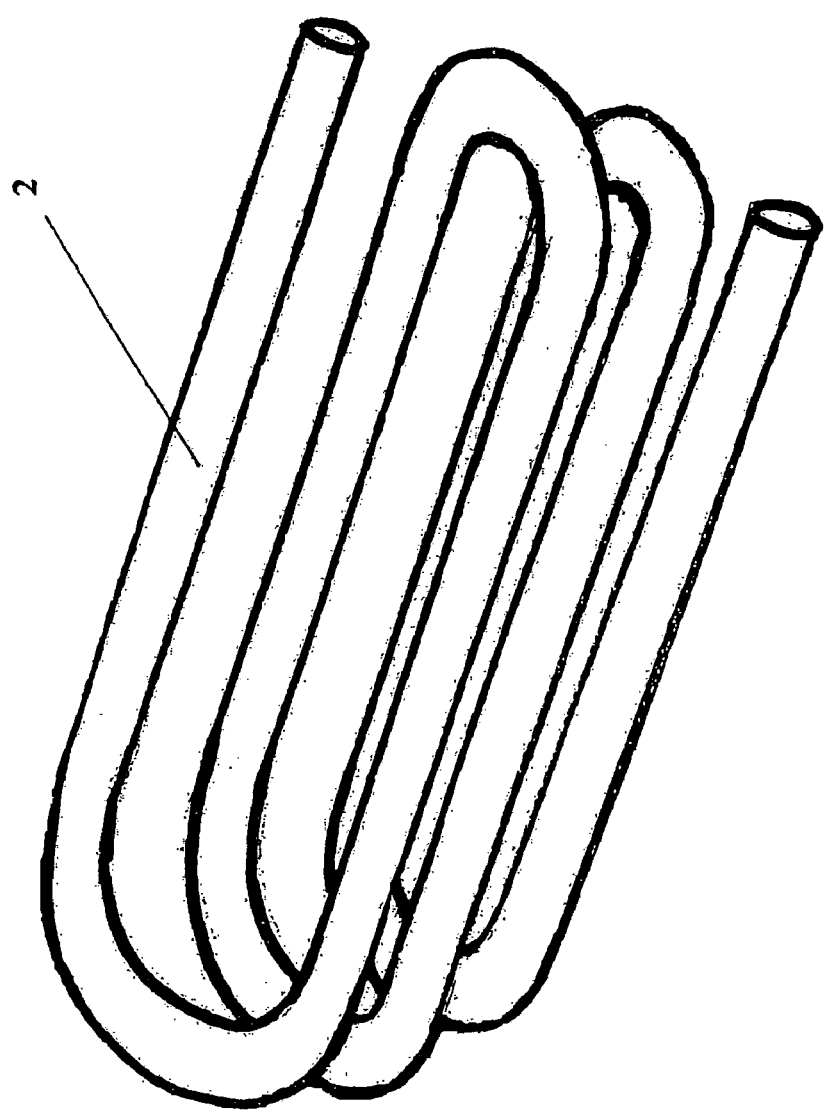
FIG. 2 is a schematic layout drawing for the present Super Tube invention showing a bending angle of 900° from the original orientation with five U (180°) turns.
Figure 3:
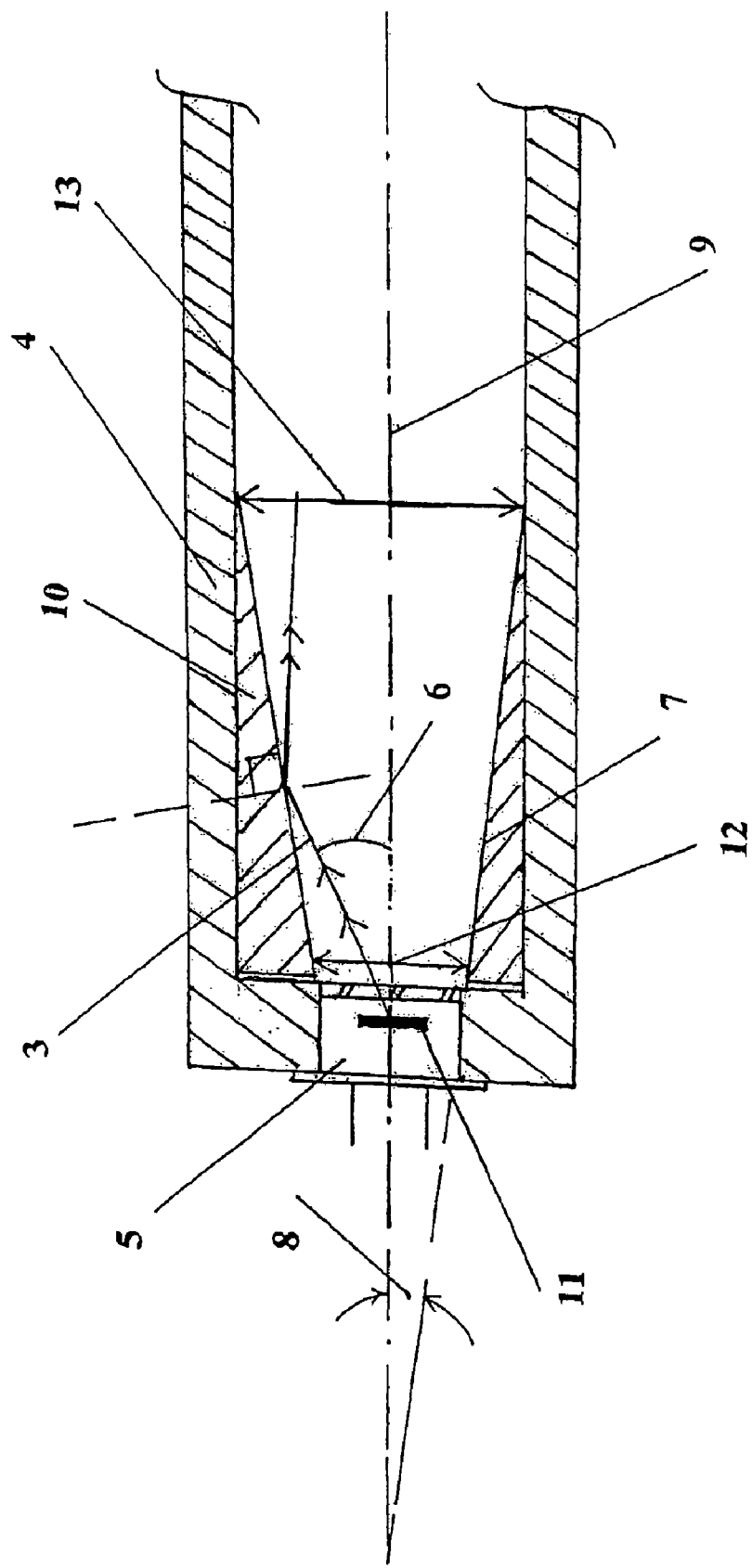
FIG. 3 shows the use of a conical mirror installed in front of the infrared source in order to limit the launching angle of the radiation emanating from it to <20° with respect to the longitudinal axis of the Super Tube.

Depending upon the path length requirement together with an overall dimensional restriction for a particular sensor, the number of U bends forming the Super Tube can be increased to meet a particular demand. FIG. 2 shows a Super Tube 2 that possesses a total of 5 U bends. In this case for the same R=1.25" and L=12" as before, the path length of the Super Tube 2 as depicted in FIG. 2 is close to 3 meters or nine feet. It is especially preferred, for ease of manufacture, that the two ends of the Super Tube are in roughly the same plane and that the bends be U bends (i.e., 180° bends), but this is not required. With reference to FIG. 3, for the Super Tube to work as designed, radiation 3 radiating into this long sample chamber 4 from infrared source 5 having many U (180°) bends must be able to "turn" corners inside with relative ease to thereby propagate inside it without any significant losses in intensity.

The mechanism and efficiency of radiation propagating along a curved tube such as a circle, a U (180°) or right angle (90°) or a combination thereof is quite different from those propagating along a straight section of a tube. In both cases, radiation has to reflect repeatedly forward within the smooth inner walls of the tube in order to reach the detector, its intended target. For radiation propagating along a straight section of a tube, the result is simple and deterministic. However, for radiation propagating along a curved tubing, the result can be haphazard and unpredictable. In this case, the angle of incidence of the impinging radiation upon the inner wall surface plays a crucial role in determining whether the radiation will continue to go forwards, trapped into stationery resonant reflections or reversing its reflection direction going backwards altogether. Depending upon the size of the tube, there exists a critical angle of incidence for the impinging radiation above which the reflecting and forward-going radiation will reverse its direction along the tube and go backwards. Thus, in order to ensure that the radiation introduced into a waveguide sample chamber having a structure other than a simple straight section, the entrance angle of incidence, which depends upon the tube diameter, must be correctly designed and taken into consideration.

The present invention addresses this problem by reducing the angle of incidence 6 for radiations emanating from a quasi-blackbody infrared source 5 with a reflecting conical surface 7 having an inclined angle 8 to the longitudinal axis 9 of the Super Tube of ~10° as depicted in FIG. 3. In order to provide this symmetrical conical reflecting surface 7, a hollow conical mirror 10 (see FIG. 3) is installed very closely to emitting surface 11 of infrared source 5. This hollow conical mirror 10 has a polished inner surface 7 to provide a high reflectivity for incident radiation 3 emanating from infrared source 5. Aperture 12 of conical mirror 10 facing infrared source 5 virtually accepts all radiations from it. The opposite aperture 13 of conical mirror 10 matches the inner diameter R of the Super Tube.

Since most infrared sources are quasi-blackbodies, the radiation pattern in a hemisphere follows closely to that of the Lambertian distribution. The Lambertian distribution of an infrared source specifies the magnitude of its spectral radiant emittance radiating into an hemisphere at any point in space as a function of the Euler angles subtended by the point at the geometrical center of the source. From the consideration of their subtended solid angles at the source, both obtuse (grazing) and normal (perpendicular to the source surface) direction radiations are much weaker than those radiating at angles between 30-60° as measured from the normal to the source's surface. Thus, a significant amount of radiation from an infrared source entering the "wave-guide" sample chamber or the Super Tube will normally have incident angles ranging from 30 to over 60°. Radiations traveling in a tube having this range of incident angles will not be able to turn circular corners having a relatively small radius (<2.0") efficiently. The same holds true for traversing a 180° U turn. However, the installation of the hollow conical mirror 10 (see FIG. 3) effectively reduces the magnitude of the "bouncing angle" for radiation emanating from the source to approximately <20° thereby greatly increasing its throughput as the radiation traverses the bending curves of the Super Tube.

Figure 4:
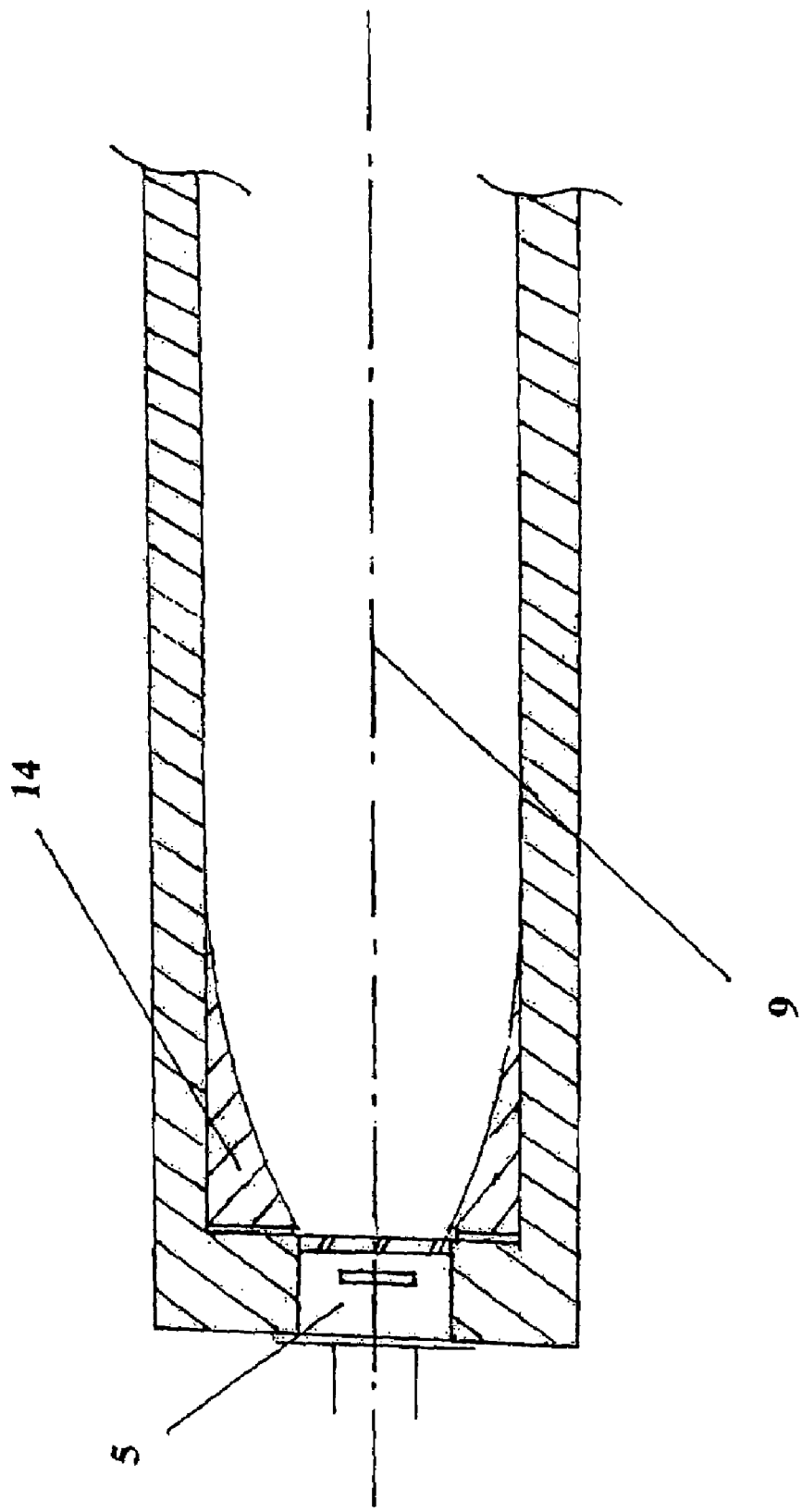
FIG. 4 shows the use of a parabolic mirror in front of the infrared source in order to limit the launching angle of the radiation emanating from it to <20° with respect to the longitudinal axis of the Super Tube.

Another approach to limit the launching angle for radiations emanating from an infrared source for the Super Tube is to install a parabolic mirror in front of the source as shown schematically in FIG. 4. In FIG. 4, source 5 will be located very close to the focus of parabolic mirror 14 so that most of the radiation from source 5 will be quasi-focused into an approximately parallel beam hugging longitudinal axis 9 of the Super Tube 4; however, such radiation must not be a beam that is parallel, such as what might be obtained through use of a laser, because such a beam would hit the wall of the first bend and bounce back out of the Super Tube, not propagate within the Super Tube. Accordingly, the "bouncing angle" for radiation emanating from the source should ideally be greater than 0° and less than approximately 20°.

Figure 5:
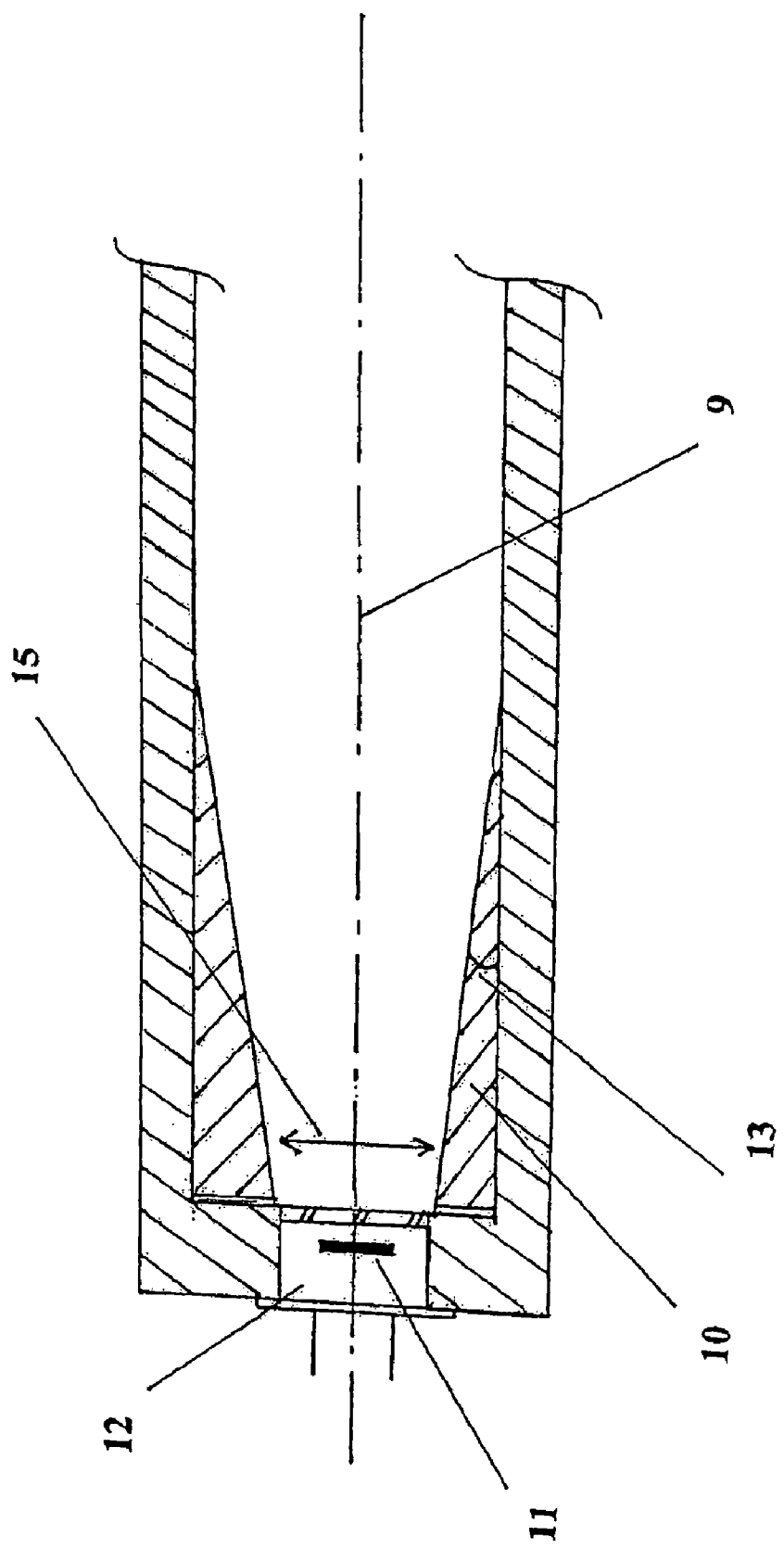
FIG. 5 shows the use of a conical mirror installed just in front of the infrared detector serving as a radiation concentrator in order to condense the radiation from the source onto the detector.

Contrary to the disclosure of the U.S. Pat. No. 5,696,379 issued to Stock (1997), the current invention is a 3-dimensional configuration such as stacking a number of U-bends upon themselves much like forming a column of paper clips with one on top of the other as exemplified in FIGS. 1 and 2 as examples. For the current Super Tube invention to work, another problem that needs to be addressed is how to restore some of the inevitable losses that the radiation, emanating from the infrared source, suffers as it traverses the 3-dimensional Super Tube. Since the sensitive area of the infrared detector is smaller than the internal diameter of the Super Tube, another hollow conical mirror can be used to focus down the extent of the incoming radiation to match the sensitive area of the detector as illustrated in FIG. 5. Unlike the situation described earlier in the use of a conical mirror to limit the launching angle of radiations emanating from the infrared source 5 (see FIG. 3), aperture 15 of conical mirror 10 (see FIG. 5) is only slightly larger than the sensitive area 11 of infrared detector 12. It is important to point out that the vertical angle 13 of conical mirror 10 with respect to the longitudinal axis 9 of the Super Tube must not be more than ~10° otherwise the incident radiation might reverse itself in direction and miss the detector altogether.

The final and extraordinarily difficult problem facing the Super Tube is a problem whose existence to date has not even been identified nor properly addressed by the NDIR gas sensor community, namely, the interference of the measurement of very weak absorbing gases, or gases that need to be detected down to very low levels (e.g. ppm-ppb ranges) or both by the presence of an unpredictable quantity of water vapor in the ambient air.

Let us briefly explain why water vapor interference is such a nasty problem for making very low concentration measurements for weakly absorbing gases when using the NDIR gas detection technique. First of all, apart from its prominent infrared absorption bands at 1.87µ, 2.67µ, 3.2µ and 6.27µ, water vapor has numerous weaker absorptions literally everywhere throughout the middle infrared spectrum (2.0µ-16µ). For measurement of gas concentrations such as CO2, methane etc. in the hundreds of ppm range using the NDIR technique, such weak absorptions of water vapor can be ignored because its interference, even within the absorption band of the gas in question, is equivalent to only a few ppm's and hence relatively small. However, for the measurement of very low concentration of gas species (ppb-ppm ranges) such as ethylene (C2H4), the interference of these weak but fluctuating water vapor absorptions within the pass band of C2H4 on the actual gas measurement is nevertheless significant. Even though its effect is also equivalent to just a few ppm's, its magnitude is comparable to the level of the gas measurement itself. For this reason, the water vapor interference must be corrected or compensated for. The current invention uses what is called an "in-situ" water vapor interference correction methodology to overcome this problem. Such a method actually measures the amount of water vapor present in the sample chamber with the use of a separate and in-situ calibrated detector so that the interference effect can be quantitatively deducted from the measured signal. As will be expounded below, such a methodology is feasible only with the advent of the current Super Tube sample chamber configuration and is therefore uniquely complementary to the current invention.

Apart from some very strong infrared absorbing bands, water vapor also has very weakly absorbing bands throughout the entire infrared region (2-16μ). In fact, that is the reason why water vapor is such a bother, but only in very special situations when very low concentration of gases need to be detected as mentioned above. However, there is a silver lining behind it. Because of the fact that the absorption is so weak in the regions other than its own strong absorbing bands, the concentration of water vapor can be measured almost anywhere provided that there are no known absorption bands for other gases (including the gas in question) present. In other words, whereas the spectral filter for the gas measurement has to be carefully selected, the spectral filter for the water measurement can be readily chosen as long as the filter band does not coincide with any known absorption bands of gases in the atmosphere. Thus it is possible to detect the actual presence of water vapor within a particular absorption band designed to measure gas X by providing a second detector that will simultaneously measure only water vapor and nothing else. Since the absorbing band for gas X also measures water vapor, the measurement of only water vapor by another detector could be used to subtract out the contribution of water vapor in the gas X measurement channel.

Figure 6:
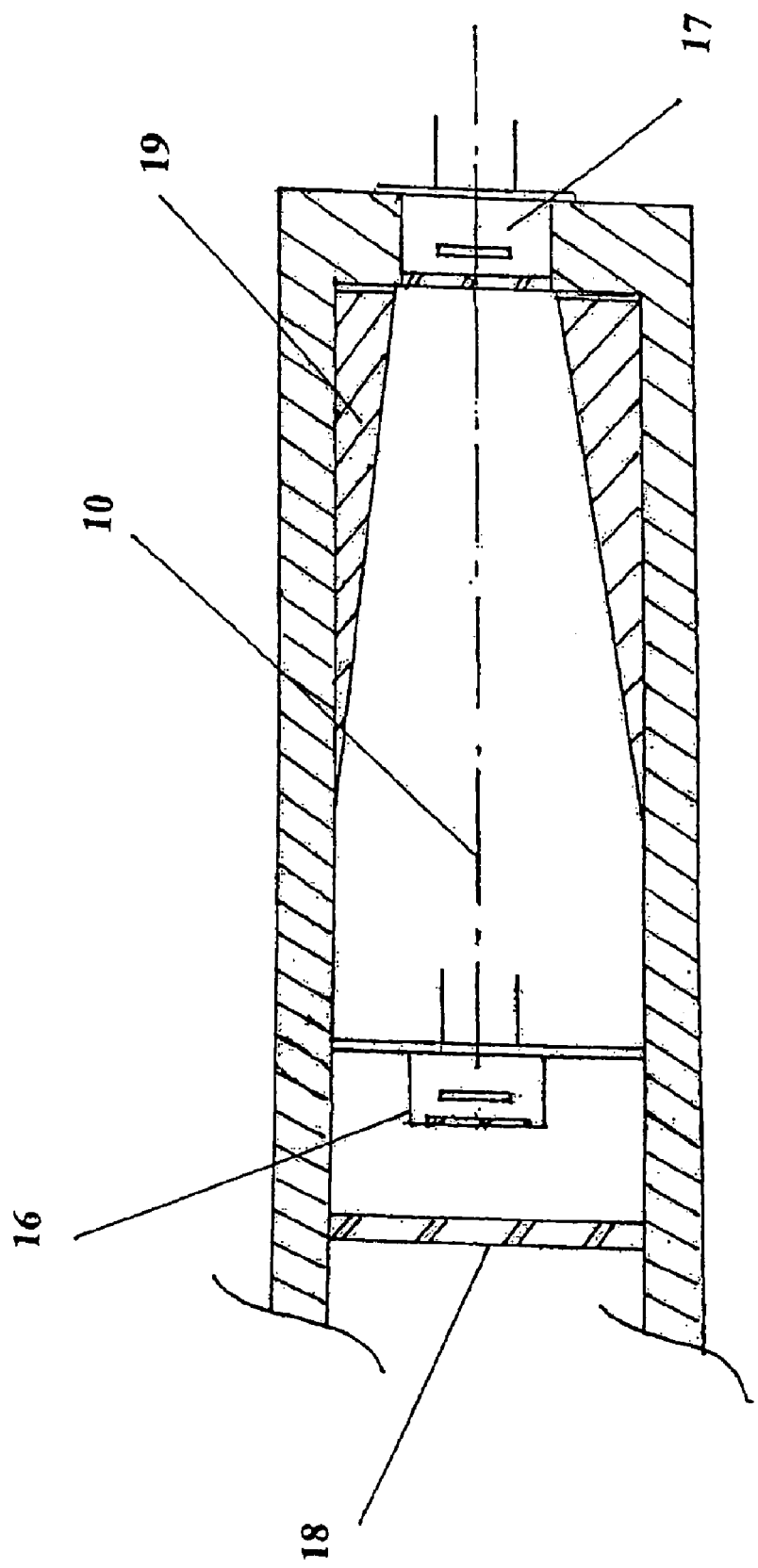
FIG. 6 shows the optical arrangement installed within the Super Tube near the detector end for creating two in-line detectors one of which is used to measure water vapor in order to provide real time in-situ correction for water vapor interference.

The Super Tube's unique sample chamber configuration provides a very convenient way to set up an optical arrangement for installing a second detector in line with the main "gas" detector for the measurement of water vapor as illustrated in FIG. 6. As shown in FIG. 6, both the gas detector 16 and the second water vapor detector 17 are housed behind an infrared window 18 in a detector chamber. Window 18 is used to eliminate any thermal influence from the flowing gas sample on the performance of the detectors during operation. As shown in FIG. 6, the front or "gas" detector 16 is structurally suspended in the middle of the Super Tube but does not totally obscure the second or back detector 17 from the incident radiation of the infrared source. To improve the collection efficiency of radiation for the back detector 17, a suitably designed conical mirror 19 can be installed in front of it as shown in FIG. 6. Despite the functionally negligible difference in radiation collection efficiency for the two detectors, both of them share substantially the same sample chamber environment as far as gas measurement is concerned. While the ambient gas sample entering the sensor contains both the "gas" to be measured and also a certain unknown amount of water vapor, the front detector will measure the influence of both gas species on its output whereas the back detector measures only the influence of the water vapor present in the entering gas sample. Thus, if the output influence of the second detector is subtracted from that of the first, the interference of water vapor on the "gas" measurement is effectively taken into consideration or eliminated. (Or, of course, the order of the detectors could be reversed and the first detector could be used to measure the influence of water vapor while the second detector could be used to measure the influence of the gas species to be detected.)

Figure 7:
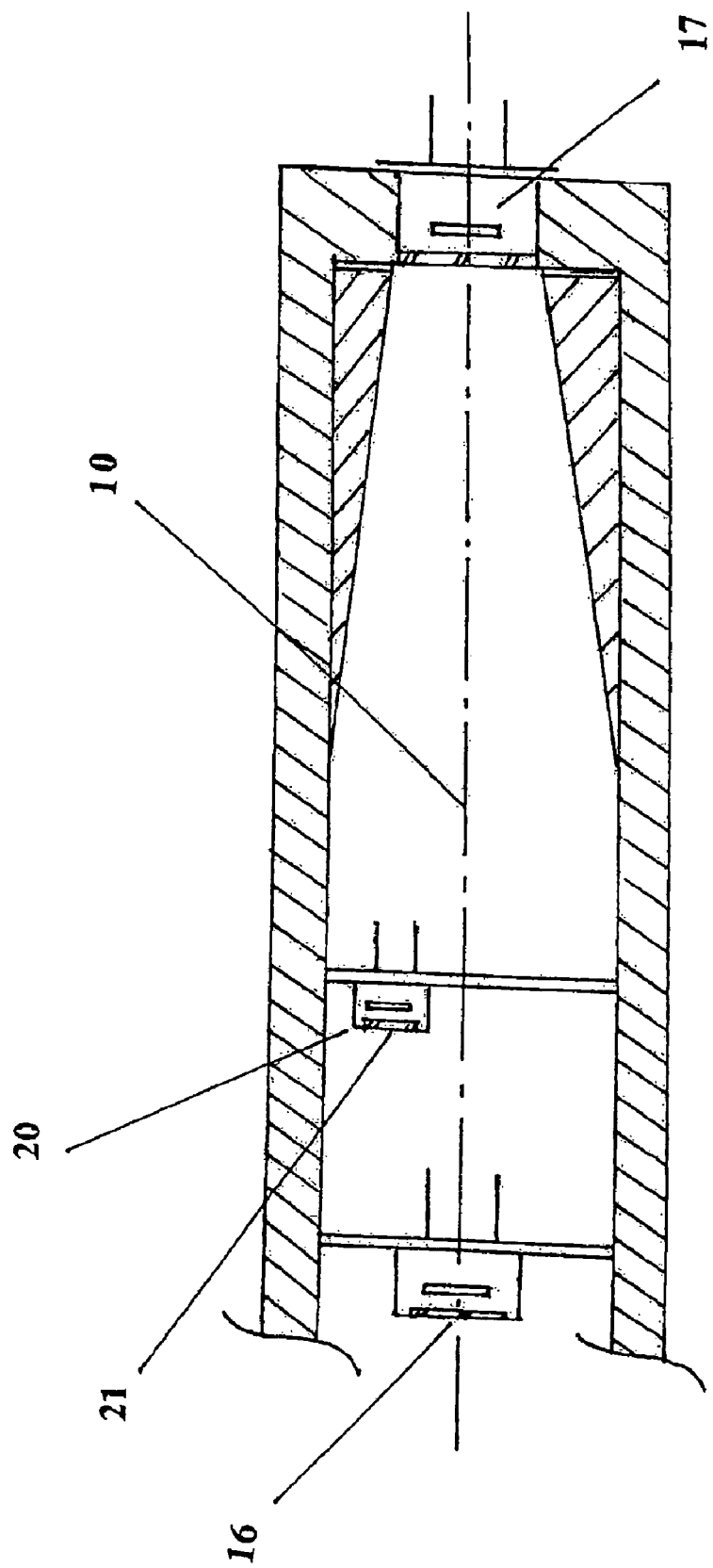
FIG. 7 shows an optical arrangement installed within the Super Tube near the detector end for creating two or more in-line detectors that will provide the sensor with a multi-gas detection capability.

The optical arrangement concept disclosed above in the use of two in-line detectors for correcting the interference of water vapor in "gas" measurement can readily be extended to render the sensor into one that can detect multiple gas species. Such an optical arrangement is depicted in FIG. 7. With the exception of the front-most detector 16 and the rear-most detector 17 one or more detectors can be mounted off-axis so as not to impede the incident radiation from reaching the rear-most detector 17 but allowing some radiation to incident on itself. (Also, the other detectors could also be mounted off-axis, but this is not preferable because such an arrangement would be less efficient.) As shown in FIG. 7, a third detector 20 with an appropriate spectral filter 21 for detecting gas species Y, represents another gas detection means when it is mounted off the axis 10 and behind the front-most detector 16. Similarly, more detectors with appropriate filters can be mounted off-axis in front of the rear-most detector 17. Thus, this optical arrangement, which is unique to the current Super Tube sample chamber, is capable of rendering the sensor with multiple gas species detection capability.

The optics of the current Super Tube invention provide yet another very important sensor performance enhancement characteristic. Because the sensor optics comprises only a reflective hollow tube and radiation from the infrared source is made to travel forwards from one end of the tube to reach one or more detectors at the other end, there is no inherent restriction as to how much incident power from the source can be "pumped" into the Super Tube provided adequate heat-sinking means is available. In other words, the Super Tube allows, at least in principle, as much radiation as is needed to be used for the detection of one or more gases. Since the detectivities of the sensor detectors are not affected, the overall signal-to-noise (S/N) can be boosted at will. The only limitation appears to be the added implementation cost for the sensor.

Figure 8:
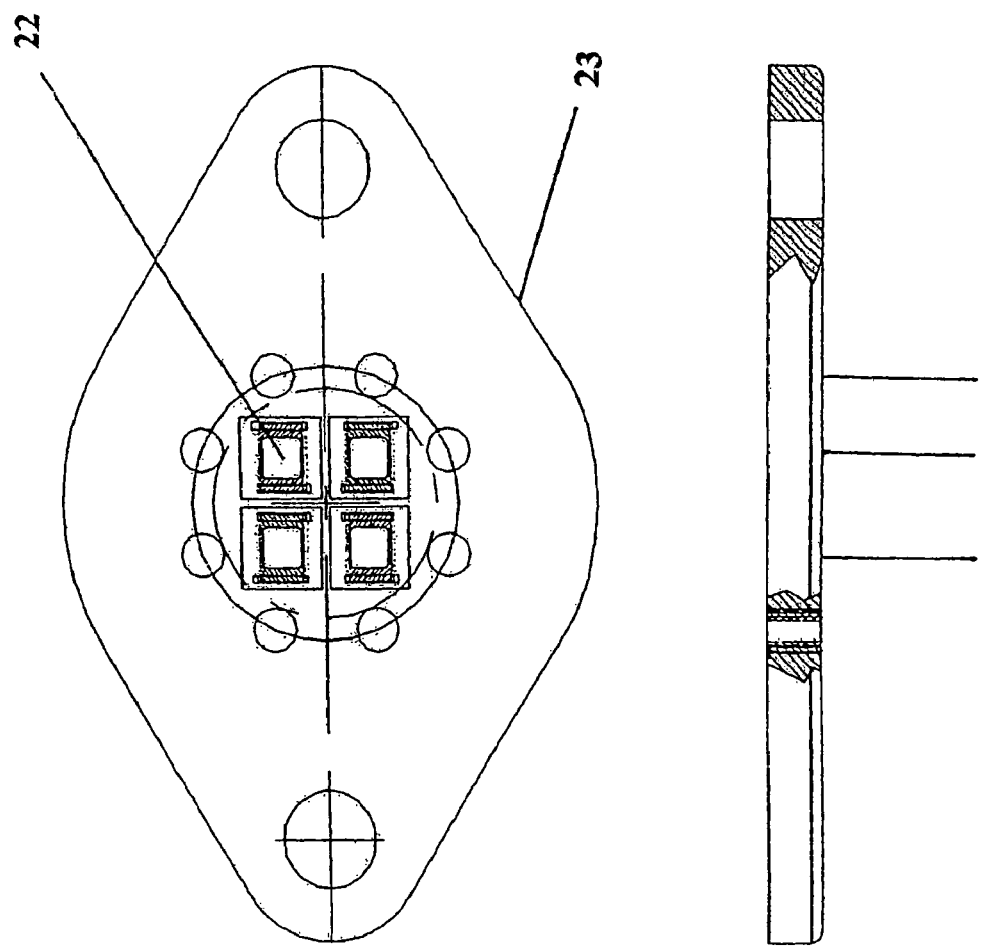
FIG. 8 shows a packaging scheme for mounting four standard infrared sources onto a special TO8 header.

FIG. 8 shows one packaging scheme for the Super Tube infrared source that houses four regular blackbody sources thus boosting the incident radiation by a factor close to four. With reference to FIG. 8, four blackbody sources 22 are die-attached on to one single T08 header 23 with a protective can (not shown). The special T08 header 23 allows the extra heat generated by the sources to be adequately dissipated to a heat sink (not shown) and its surroundings. It can readily be seen that any reasonable number of similar blackbody sources (>4) can be packaged to a custom header if more power is required.

It can be seen from the discussion above that the current Super Tube invention is capable of providing long path lengths for the detection of trace gases having a very weak infrared absorption band or required to be detected down to ppb-ppm ranges within a relatively compact space. Furthermore, the current invention offers great robustness and a low-cost implementation when applied to either NDIR or TDLAS type transportable gas analyzers.

While the invention has been described herein with reference to certain examples, those examples have been presented for illustration and explanation only, and not to limit the scope of the invention. Additional modifications and examples thereof will be obvious to those skilled in the art having the benefit of this detailed description. For example, while the Super Tube has been depicted in the drawings and discussed above as having a circular cross-section, it need not only have such geometry; instead, the Super Tube can have a cross section in many different geometries, such as a square, so long as it functions as a hollow waveguide. In addition, several detectors can be combined in one physical package and the Super Tube will also be useful in certain applications where only one detector is required. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. An NDIR method for detecting the concentration of a gas species X, comprising:
   emitting infrared radiation from a source into a sample cell comprised of a hollow waveguide with a plurality of bends that are collectively greater than 180 degrees in three dimensions, said infrared radiation being quasi-focused into a beam with an angle of incidence between greater than approximately 0° and approximately 10° relative to a longitudinal axis of a first linear segment of the sample cell proximate the source;
   detecting a first signal at a first detector located in a detector chamber of the waveguide:
   detecting a second signal at a second detector located in the detector chamber; and
   using the second signal to adjust the first signal for detecting the concentration of the gas species X;
   wherein one of the first and second signals is based upon a first absorption band for gas species X while the other of said signals is based upon a second absorption band chosen to detect water which does not coincide with any known absorption bands of gases in the sample cell.

2. The method of claim 1, wherein the concentration of gas species X detected is less than 100 parts per million ("ppm").

3. The method of claim 1, wherein the concentration of gas species X detected is less than 1 ppm.

4. The method of claim 1, wherein the plurality of bends are collectively greater than 360 degrees in three dimensions.

5. The method of claim 1, wherein said infrared radiation is quasi-focused into the beam by a conical reflective surface having an inclined angle to the longitudinal axis of approximately 10 degrees and the conical reflective surface is installed proximate an emitting surface of the infrared source.

6. The method of claim 1, wherein said infrared radiation is quasi-focused into the beam by a parabolic mirror.

7. The method of claim 1, comprising the further step of:
   focusing said infrared radiation after it has traveled through substantially all of the waveguide and as it approaches the first detector.

8. The method of claim 7, wherein the radiation is focused as it approaches the first detector by a conical mirror with a vertical angle with respect to the longitudinal axis of the detector chamber of not more than approximately 10 degrees.

9. The method of claim 1, comprising the further step of:
   focusing said infrared radiation between the first detector toward the second detector.

10. The method of claim 1, wherein one of the first and second detectors are offset relative to the other of said detectors in the detector chamber and the first and second detectors are positioned in-line on a single detector axis.

11. The method of claim 1, comprising the further steps of:
    detecting a third signal at a third detector located in the detector chamber between the first and the second detectors; and
    using the second signal to adjust the third signal for detecting the concentration of a gas species Y;
    wherein the third signal is based upon a third absorption band for gas species Y.

12. The method of claim 11, wherein the third detector is mounted off the single detector axis.

13. The method of claim 12, comprising the further steps of:
    focusing said infrared radiation between the first detector toward the second detector; and
    focusing said infrared radiation between the second detector and the third detector.

14. The method of claim 1, comprising the further step of:
    using a plurality of infrared sources to emit infrared radiation into the sample cell.

15. An NDIR method for detecting a concentration of a gas species X which is less than 100 ppm, comprising:
    emitting infrared radiation from a source into a sample cell comprised of a hollow waveguide with a plurality of bends that are collectively greater than 360 degrees in three dimensions, said infrared radiation being quasi-focused into a beam with an angle of incidence between greater than approximately 0° and approximately 10° relative to a longitudinal axis of a first linear segment of the sample cell proximate the source;
    focusing said infrared radiation after it has traveled through substantially all of the waveguide and as it approaches the first detector;
    detecting a first signal at a first detector located in a detector chamber of the waveguide;
    detecting a second signal at a second detector located in the detector chamber; and
    using the second signal to adjust the first signal for detecting the concentration of the gas species X;
    wherein one of the first and second detectors are offset relative to the other of said detectors in the detector chamber; and
    wherein one of the first and second signals is based upon a first absorption band for gas species X while the other of said signals is based upon a second absorption band chosen to detect water which does not coincide with any known absorption bands of gases in the sample cell.

16. The method of claim 15, wherein the concentration of gas species X detected is less than 1 ppm.

17. The method of claim 16, comprising the further step of:
    focusing said infrared radiation between the first detector toward the second detector.

18. The method of claim 17, comprising the further steps of:
    detecting a third signal at a third detector located in the detector chamber between the first and the second detectors; and
    using the second signal to adjust the third signal for detecting the concentration of a gas species Y;
    wherein the third signal is based upon a third absorption band for gas species Y.

19. The method of claim 18, wherein the concentration of the gas species Y is less than 1 ppm.

20. The method of claim 19, comprising the further step of:
    using a plurality of infrared sources to emit infrared radiation into the sample cell.

* * * * *